US011291862B2

(12) United States Patent
Dorohovich et al.

(10) Patent No.: US 11,291,862 B2
(45) Date of Patent: Apr. 5, 2022

(54) MEDICAL SOURCE OF NEUTRONS, NUCLEAR REACTOR FOR A MEDICAL NEUTRON SOURCE, AND METHOD OF APPLICATION OF A MEDICAL NEUTRON SOURCE

(71) Applicant: Research and Development Center for Innovations, Moscow (RU)

(72) Inventors: Sergey L. Dorohovich, Obninsk (RU); Yuriy A. Kazanskiy, Obninsk (RU); Yuriy A. Kurachenko, Obninsk (RU); Larion A. Lebedev, Moscow (RU); Valeriy A. Levchenko, Obninsk (RU); Aleksandr V. Levchenko, Obninsk (RU); Evgeniy S. Matusevich, Obninsk (RU)

(73) Assignee: RESEARCH AND DEVELOPMENT CENTER FOR INNOVATIONS, Moscow (RU)

( * ) Notice: Subject to any disclaimer, the term of this patent is extended or adjusted under 35 U.S.C. 154(b) by 743 days.

(21) Appl. No.: 15/934,669

(22) Filed: Mar. 23, 2018

(65) Prior Publication Data

US 2018/0207449 A1    Jul. 26, 2018

Related U.S. Application Data

(63) Continuation of application No. PCT/RU2016/000641, filed on Sep. 23, 2016.

(30) Foreign Application Priority Data

Sep. 24, 2015    (RU) .......................... RU2015140722

(51) Int. Cl.
*A61N 5/10*    (2006.01)
*G21C 1/00*    (2018.01)
(Continued)

(52) U.S. Cl.
CPC ............. *A61N 5/1048* (2013.01); *A61N 5/10* (2013.01); *A61N 5/1001* (2013.01); *G21C 1/00* (2013.01);
(Continued)

(58) Field of Classification Search
CPC ...... A61N 5/10; A61N 5/1001; A61N 5/1048; A61N 2005/1019; A61N 2005/109; G21C 15/18; G21C 1/00; G21C 1/30
See application file for complete search history.

(56) References Cited

U.S. PATENT DOCUMENTS 4,326,922 A * 4/1982 Ferrari .................. G21C 3/326
                                                  376/435
5,433,693 A * 7/1995 Ott .......................... A61N 5/10
                                                  600/1
(Continued)

FOREIGN PATENT DOCUMENTS

RU          2141860 C1      11/1999
RU          2442620 C2       2/2012
WO       1994015670 A1       7/1994

OTHER PUBLICATIONS

Townes, B. M., and J. W. Hilborn. The SLOWPOKE-2 reactor with low enrichment uranium oxide fuel. No. AECL-8840. Atomic Energy of Canada Ltd., 1985. <https://inis.iaea.org/collection/NCLCollectionStore/_Public/17/062/17062901.pdf>.*
(Continued)

*Primary Examiner* — Lily C Garner
(74) *Attorney, Agent, or Firm* — Patentbar International PC

(57) ABSTRACT

A coolant having a set temperature is fed into the nuclear reactor core of a medical neutron source, which is in a subcritical state. The nuclear reactor core is transitioned from the subcritical state to a critical state until the nominal power of the nuclear reactor is achieved. A neutron output
(Continued)

channel is opened in order to conduct a neutron therapy session, and the operation of the reactor is maintained at nominal power while the neutron therapy session is conducted. At the end of the session, the neutron output channel is closed at the same time as the reactor core is transitioned to a subcritical state. The temperature of the coolant entering the core is maintained unchanged and equal to a set temperature, both when the core is transitioned to a critical state and during the operation of the nuclear reactor at nominal power.

16 Claims, 6 Drawing Sheets

(51) Int. Cl.
    *G21C 1/30*     (2006.01)
    *H05H 3/06*     (2006.01)

(52) U.S. Cl.
    CPC ............... *G21C 1/30* (2013.01); *H05H 3/06* (2013.01); *A61N 2005/109* (2013.01); *Y02E 30/30* (2013.01)

(56) References Cited

U.S. PATENT DOCUMENTS

| | | | | |
|---|---|---|---|---|
| 5,490,191 | A * | 2/1996 | Christiansen | G21C 3/32 376/434 |
| 6,674,829 | B1 * | 1/2004 | Skold | A61N 5/10 250/492.1 |
| 10,854,341 | B2 * | 12/2020 | Lebedev | G21C 1/022 |
| 2002/0085660 | A1 * | 7/2002 | Nakamaru | G21C 7/08 376/283 |
| 2014/0334595 | A1 * | 11/2014 | Bashkirtsev | G21C 3/326 376/419 |
| 2015/0243384 | A1 * | 8/2015 | Kwon | G21C 15/18 376/282 |
| 2018/0350474 | A1 * | 12/2018 | Scott | G21C 3/3245 |

OTHER PUBLICATIONS

McCall, M. J., and M. Pierre. "A Feasibility Study of the SLOWPOKE-2 Reactor as a Neutron Source for Boron Neutron Cancer Treatment." (2000). <http://www.nuceng.ca/univcomm/studconf2000/paper1-2-mccall.pdf>.*

Aleksandrov, A. P. "Development of uranium-graphite channel reactors in the USSR." Soviet Atomic Energy 43.5 (1977): 985-992. <https://link.springer.com/content/pdf/10.1007/BF01118547.pdf>.*

International Search Report from PCT/RU2016/000641, filed Sep. 23, 2016, dated Jan. 26, 2017.

Barth, Rolf F. et al., Boron Neutron Capture Therapy of Cancer: Current Status and Future Prospects, Clin. Cancer Res., Jun. 1, 2005, v. 11, No. 11, pp. 3987-4002.

INEEL Advanced Radiotherapy Research Program Annual Report 2001, J.R. Venhuizen, Apr. 2002, Idaho National Engineering and Environmental Laboratory, Bechtel BWXT Idaho, LLC.

Tsyb A.F., et al., Neutrons in the Treatment of Malignant Neoplasms, 2003, Chapters 3 and 8, Obninsk.

Zaitsev K., et al., NCT at the MEPHI Reactor, International Journal of Nuclear Energy and Technology, 2004, pp. 82-98, vol. 1.

Hanan N.A., et al., A neutronic feasibility study for LEU conversion of the Brookhaven Medical Research Reactor (BMRR), 1997 International Meeting on Reduced Enrichment for Research & Test Reactors, Jackson Hole, Wyoming, USA, Oct. 5-10, 1997.

Thomas H. Newton, Jr., Preliminary investigation of the use of monolithic U-Mo fuel in the MIT Reactor, 2003 International Meeting on Reduced Enrichment for Research and Test Reactors, Chicago, Illinois, Oct. 5-10, 2003.

McCall M.J., et al., A Feasibility Study of the SLOWPOKE-2 Reactor as a Neutron Source for Boron Neutron Cancer Treatment, 25th CNS/CNA Annual Student Conference McMaster University, Hamilton, Ontario, Mar. 10-11, 2000.

Oregon State University Radiation Center and TRIGA Reactor, Annual Report Jul. 1, 2002-Jun. 30, 2003, Oct. 2003.

Litjaev, V. M. et al., Medical irradiation facility based on fluid fuel reactor with low power, Advances in Neutron Capture Therapy, 1997, vol. 1, pp. 396-399, Medicine and Physics, Elsevier Science B.V.

* cited by examiner

MEDICAL SOURCE OF NEUTRONS, NUCLEAR REACTOR FOR A MEDICAL NEUTRON SOURCE, AND METHOD OF APPLICATION OF A MEDICAL NEUTRON SOURCE

RELATED APPLICATIONS

This Application is a Continuation application of International Application PCT/RU2016/000641, filed on Sep. 23, 2016, which in turn claims priority to Russian Patent Applications No. RU2015140722, filed Sep. 24, 2015, both of which are incorporated herein by reference in their entirety.

FIELD OF THE INVENTION

The invention relates to the field of nuclear physics and medicine, in particular to the radiation therapy and can be used for the realization of the neutron therapy of human malignant tumors, which found an application in the treatment of oncological diseases.

BACKGROUND OF THE INVENTION

Radiation therapy is the main method of treatment for 70% of patients with oncological diseases. In many cases, irradiation of tumors with photons and electrons in the treatment of cancer is not very effective. According to various estimates, the proportion of such patients ranges from 10 to 30% of all patients who receive radiotherapy. The irradiation with neutrons possessing a number of radiobiological advantages in comparison with photons and electrons can help them.

In the therapy of malignant tumors, both fast neutrons with the energy from the fraction of MeV to tens of MeV (the so-called fast neutron therapy—FNT) and epithermal with the energy in the range from several eV to tens of keV (neutron-capture therapy—NCT) are used.

Currently, NCT appears to be the most promising, as it focuses on the treatment of such types of malignant tumors that are practically not amenable to treatment by other methods, for example, brain tumors (glioblastoma multiforme and anaplastic astrocytoma), and melanoma. Estimates show that several hundred thousand people suffer from these diseases around the world, and NCT is indicated to them.

Neutron-capture therapy of tumors is a complex, multi-component medical technology that poses high demands on the parameters of the neutron beam used for irradiation, especially on its intensity.

The neutron beam used for NCT treatment is "ideal" if it contains a small fraction of thermal neutrons, a large fraction of epithermal neutrons with energies from 0.4 eV to 10 keV, and a small contribution of fast neutrons. It is highly desirable to change the spectrum of epithermal neutrons depending on the depth of the tumor location.

Installations capable of providing the required epithermal neutron flux density should act as sources for NCT. The required spectrum of epithermal neutrons can be formed behind a filter several dozen centimeters thick. However, in order to create the desired flux density, more intensive sources of fast neutrons are needed than for FNT. To the greatest extent, these requirements are met by neutron beams extracted from the core of a nuclear reactor.

The energies of neutrons withdrawn from the core of a nuclear reactor are in a very wide range—from fractions of eV to several MeV. The energy spectrum of neutrons in the beam can be changed by means of special filters and moderators, for example, to increase the average energy, removing the low-energy component (for FNT) or leaving epithermal neutrons (for NCT). Among advantages of reactor neutrons for the radiation therapy in comparison with other neutron sources there are: high energy and space-time stability of neutron beams; large geometric sections of bundles and the uniformity of the flow along the section; neutron propagation close to a monodirectional.

The large-scale introduction of the neutron therapy into the clinical practice of oncology dispensaries and radiological centers of the country now completely depends on completion of these medical facilities with intensive neutron sources, therefore the development of a small-sized nuclear reactor focused on the neutron generation for radiation therapy seems to be an urgent task. The need for such reactors for Russia only can be estimated at several dozen.

The use of several dozen nuclear reactors as neutron sources for the neutron therapy is known in the world. The characteristics of some reactor installations and their use as neutron sources for medical purposes are described in the following sources of information:
1. Tsyb A. F., Ulyanenko S. E., Mardynsky Yu. S., et al., "Neutrons in the Treatment of Malignant Neoplasms"—Obninsk: BIST, 2003.—112 p.: ill.-ISBN-5901968-09-3.
2. K. Zaitsevl, A. Portnovl, FNT at the MEPHI reactor International Journal of Nuclear Energy and Technology 2004—Vol. 1, No. 1 pp. 83-101.
3. A neutronic feasibility study for LEU conversion of the Brookhaven Medical Research Reactor (BMRR) N. A. Hanan, R. B. Pond and J. E. Matos, Argonne National Laboratory, USA Proc. 1997. International Meeting on Reduced Enrichment for Research & Test Reactors, Jackson Hole, Wyo., USA, October, 1997.
4. Thomas H. Newton, Jr. "Preliminary investigation of the use of monolithic U-Mo fuel in the NIT Reactor" 2003 International Meeting on Reduced Enrichment for Research and Test Reactors, Chicago, Ill., Oct. 5-10, 2003.
5. "INEEL Advanced Radiotherapy Research Program Annual Report 2001" J. R. Venhuizen, April 2002 Idaho National Engineering and Environmental Laboratory.
6. Oregon State University Radiation Center and TRIGA reactor Annual Report Jul. 1, 2002-Jun. 30, 2003.
7. M. J. McCall, M. Pierre, "A Feasibility Study of the SLOWPOKE-2 Reactor as a Neutron Source for Boron", 25th CNS/CNA Annual Student Conference McMaster University, Hamilton, Ontario, Mar. 10-11, 2000.
8. V. M. Litjaev, V. A. Pivovarov, N. A. Soloviev et al, "Medical irradiation facility based on fluid fuel reactor with low power".
9. Rolf F. Barth, Jeffrey A. Coderre, et al. Boron Neutron Capture Therapy of Cancer: Current Status and Future Prospects//Clin. Cancer Res. 2005, v. 11(11), p. 3987-4002.
10. Patent RU, 2141860, MPK A61N5/10, A61B6/00, G21K5/00, 1999.

The main disadvantage of the known devices is that they represent very complex and cumbersome engineering and physical facilities with a specific infrastructure that was not originally intended and is difficult to adapt for medical purposes. Even after reconstruction, these installations can not be used in clinical conditions. High-enrichment fuel is used in many of them, which does not allow their widespread use, based on the principles of non-proliferation of nuclear weapons.

As a rule, devices have more power, which negatively affects the cost of the treatment. These devices cannot work in the start-stop mode in principle, which is necessary for working with irradiated patients in an immobilized state, because it is extremely important that a well-collimated beam of neutrons enters precisely into the tumor and injure the patient's healthy tissue as little as possible.

Most of the shortcomings resulted from the fact that during designing, the mandatory principle of minimizing neutron leakage from the core was applied, and the reactor as a source of neutrons for medical purposes should be designed to have the greatest possible leakage of neutrons.

SUMMARY OF THE INVENTION

The technical result achieved in the implementation of the claimed invention consists in expanding the arsenal of technical means of neutron sources for medical purposes by creating a universal neutron source for neutron capture and fast neutron therapy, suitable for the placement directly in the clinic.

In addition, the technical result lies in increasing the safety of the neutron source by using a specialized small-sized nuclear reactor with a very low power level and a start-stop mode of operation that ensures the required neutron flux density at the site of the patient.

To be placed directly in the clinic, the source of neutrons should have economic attractiveness, in other words, to have a minimum cost of a neutron, which can be achieved due to the simplicity of the device, the maximally expedient reactivity reserve, reliability for long-term operation (at least 20-30 years), the minimum composition of the maintenance personnel working on fuel, which cannot be used as a raw material for nuclear weapons.

During the operation of the reactor of a medical neutron source, its capital investments and current costs should be offset by the cost of treatment using neutron-percussion and neutron-capture therapy, since the reactor is used only as a source of neutrons and for medical purposes alone—cancer therapy.

At the same time, the reactor should have a minimum amount of the radioactive waste (spent fuel and radioactive materials) per neutron in the therapeutic beam, which ensures the minimum possible reactor power and start-stop operation.

In order to provide a therapeutic effect during the patient's irradiation time, the source of neutrons should create for the therapy session a flux density of at least $1.10^9$ neutr.·cm$^{-2}$·c$^{-2}$ of epithermal neutrons for NCT and $5.10^8$ neutr.·cm$^{-2}$·c$^{-2}$ for FNT.

In order to meet these parameters, the reactor power should be of the order of 10 kW.

The safety of the reactor is also achieved due to a minimum operative reserve of reactivity and a minimum change in technological parameters in all modes of operation, allowing to have a reserve of reactivity below the fraction of delayed neutrons, which excludes reactive accidents.

To realize the above, the medical neutron source includes the following main elements (parts): a nuclear reactor, a collimator with a hole shaped as a truncated cone, a neutron filter, a shield, neutron exit channels (a neutron capture therapy channel, and at least one fast neutron therapy channel), a first movable gate that opens and closes the neutron-capture therapy channel, and a second movable gate that opens and closes the neutron exit channel the fast neutron therapy channel.

The nuclear reactor includes a core formed by a parallelepiped-shaped housing having a front, rear and two side walls, and a lid and bottom covering the housing from the upper and lower sides, and a neutron reflector covering the corefrom the rear, side, top and bottom sides. In a particular embodiment, the reflector may include rear, side, top and bottom reflectors.

The design of the core of the reactor is chosen flat to ensure maximum leakage of neutrons towards the filter system and the collimator. Accordingly, there is no core reflector on this side.

An upper supporting grid and a lower distancing grid are located in the housing. On the upper supporting grid, the upper ends of fuel rods are immovably fixed. The lower ends of the fuel rods are located in the lower distancing grid and are capable of vertically moving when the fuel rods thermally expand.

The channels fixed on the housing cover are located inside the core of the core, to placement the control and protection system (CPS).

There are pipes on the housing of the core of the reactor intended for the supply and removal of the thermostabilized coolant of the primary circuit.

Inside the housing, there are partitions that separate the internal volume of the casing to ensure the washing of fuel rods and channels for the placement of CPS controls by the coolant. As will be shown later, the partitions can be installed in a "staggered" order with the formation of a labyrinth channel, which ensures a uniform flow of the coolant without formation of stagnant zones.

The collimator is made of a material having a large scattering cross-section and a large atomic mass. Preferably, lead (Pb) is to be used as the collimator material.

The neutron filter is designed to form the required neutron energy spectrum in a neutron beam for the neutron capture therapy, while the filter is placed in the conical hole of the collimator in such a way that the larger diameter of the conical hole lies against the front wall of the housing of the active zone.

The neutron reflector and the collimator are located inside the protection, divided into front, back, side, top and bottom.

The neutron-capture therapy channel is formed by a hole in the frontal shield located coaxially with the conical aperture of the lead collimator.

The fast neutron therapy channel is formed by a through hole in the side shield and the side reflector.

The first reactor circuit may include a circulating pump, a coolant temperature stabilizer at the inlet to the core and a pressurizer.

In a particular embodiment of the invention, the circulation pump, the coolant temperature stabilizer, and also the pressurizer are located outside the protection.

In a particular embodiment, in the rear protection and in the rear reflector, channels can be provided for placing the pipelines of the primary circuit connected to the supply branch pipe and the outlet for the coolant to the active zone.

In a particular embodiment, the housing cover is provided with at least four channels for housing of CPS controls. In this case, the channels for the placement of CPS controls can be provided with threaded fittings with attached mechanisms for moving CPS controls Channels can be made to place the actuators of the mechanisms of moving CPS controls in the upper protection and the upper reflector.

In a specific embodiment, at least four control rods can be used as CPS controls, which are movable by the movement mechanisms of CPS controls in the channels for housing CPS controls.

One of CPS controls was chosen as the regulator for the output of the nuclear reactor core to the nominal power.

In a particular embodiment, the rear, side, top and bottom reflectors may be made of stainless steel blocks.

Preferably, the thickness of the back, side, top and bottom reflectors is selected from an interval of 290 mm to 310 mm.

It is preferable that the dimensions of the length, height and width of the parallelepiped of the inner volume of the core housing be selected from intervals of 490 mm to 498 mm, 172 mm to 180 mm and 410 mm to 490 mm, respectively.

It is preferable that the fuel rods in the core are located in a square grid whose step length is selected from an interval of 11.6 mm to 12.4 mm.

In addition, it is preferred that the invention is to use uranium dioxide ($UO_2$) with $^{235}U$ enrichment selected from an interval of 15% to 20% as fuel in fuel rods. Such enrichment is in accordance with IAEA requirements for non-proliferation of nuclear weapons.

It is also preferred that $B_4C$ be used as the absorbent material of the control rods.

To carry out the neutron therapy, a medical neutron source is used as follows. The core of a nuclear reactor in a subcritical state is supplied with a coolant at a predetermined temperature. The core of the nuclear reactor is withdrawn from the subcritical to the critical state until the nominal power of the nuclear reactor is reached.

After that, the neutron exit channel is opened to conduct a neutron therapy session. The choice of a specific neutron channel is determined by the indications of an oncological disease. During the time of the neutron therapy session, the operation of the reactor at the rated power is maintained.

At the end of the neutron therapy session, the neutron exit channel is simultaneously closed and the reactor core is transferred to the subcritical state.

The temperature of the coolant at the entrance to the core is kept constant and equal to the set temperature, both during the core withdrawal to the critical state and during the operation of the nuclear reactor at the rated power.

Water is preferably used as the heat carrier.

The set water temperature at the entrance to the core of the reactor is preferably selected from an interval of 18° C. to 24° C.

In a particular embodiment, the core is transferred from the subcritical state to the critical one and from the critical state to the subcritical state, respectively, by removing one of the CPS control rods from the core or entering the core.

The foregoing is a summary of the nature of the invention and thus may include simplifications, generalizations, inclusion and/or deletion of details, and it will therefore be appreciated by those skilled in the art that this summary of the invention is merely illustrative and does not imply any restriction.

BRIEF DESCRIPTION OF THE DRAWINGS

For a better understanding of the nature of the suggested invention, a description will now be given which is not a restrictive example of the practical implementation of the claimed group of inventions, with reference to the drawings, where:

DETAILED DESCRIPTION OF THE PREFERRED EMBODIMENTS

Figure 1:
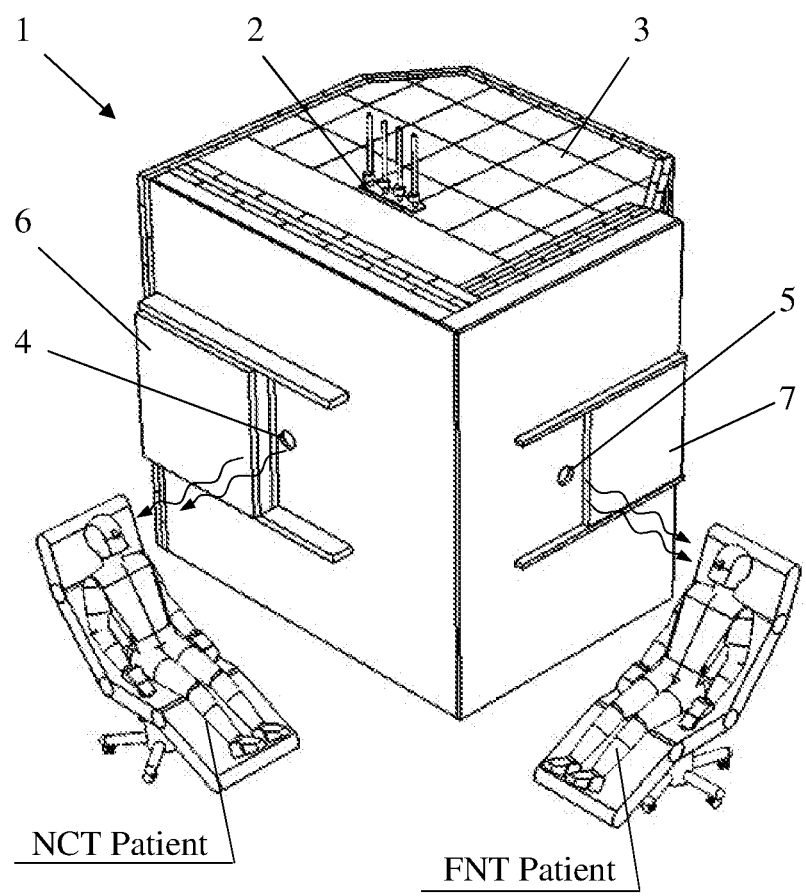
FIG. 1 shows a general view and application of a medical neutron source.

The medical source of neutrons 1 (FIG. 1) includes the following elements (parts): nuclear reactor 2, protection 3, neutron capture therapy channel 4, fast neutron therapy channel 5, first movable gate 6 for opening and closing the neutron exit channel for the neutron capture therapy, and a second movable gate 7 for opening and closing the neutron exit channel for the fast neutron therapy.

Figure 2:
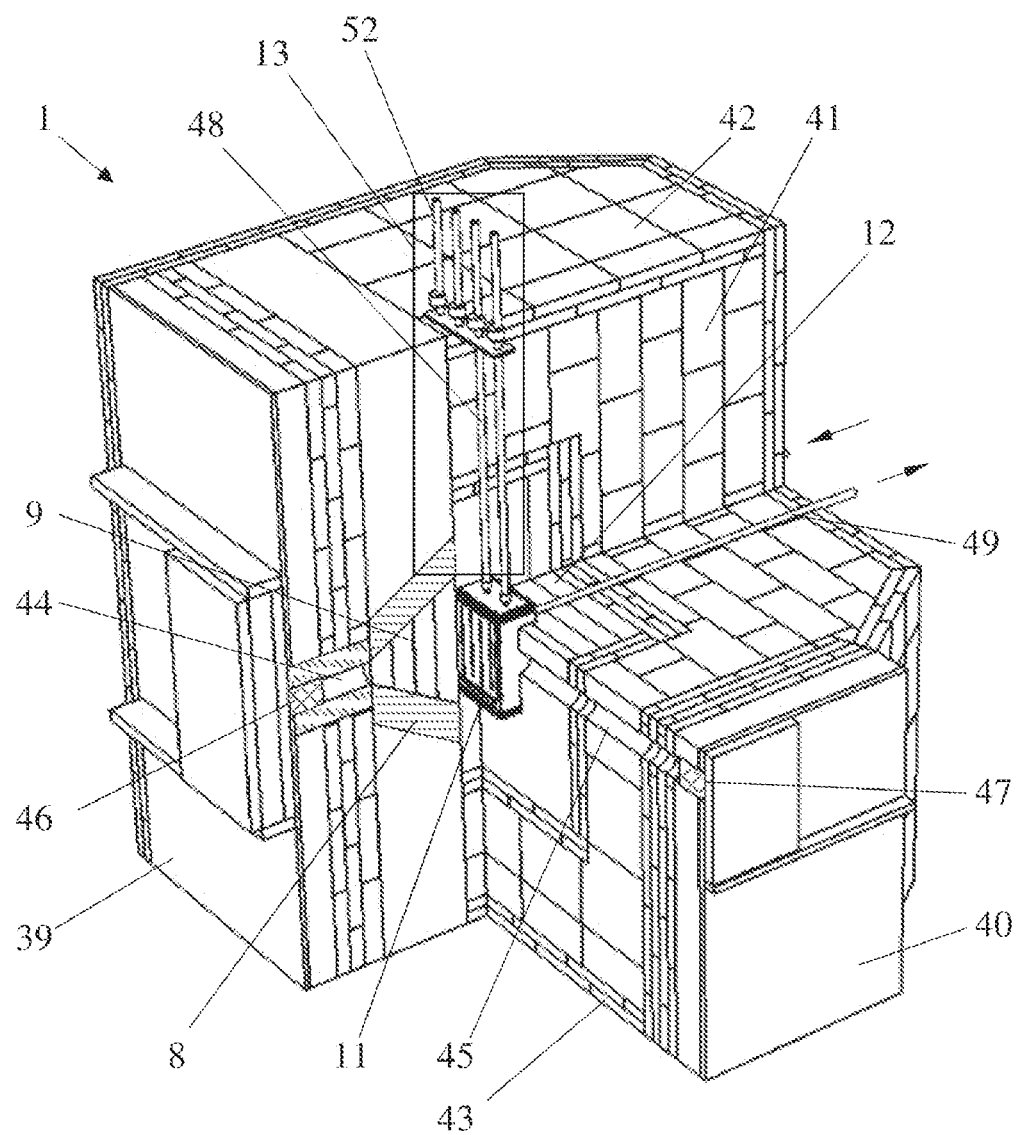
FIG. 2 shows an axonometric section of the structure of a medical neutron source.

As shown in FIG. 2, the medical neutron source 1 also includes a lead collimator 8 with a conical hole and is designed to receive a bundle of the required spectrum of a neutron filter 9 located in the conical hole of the collimator 8.

The nuclear reactor 2 of the medical neutron source comprises a hydraulic system 10, a core 11, a reflector 12 and a control and protection system 13.

Figure 3:
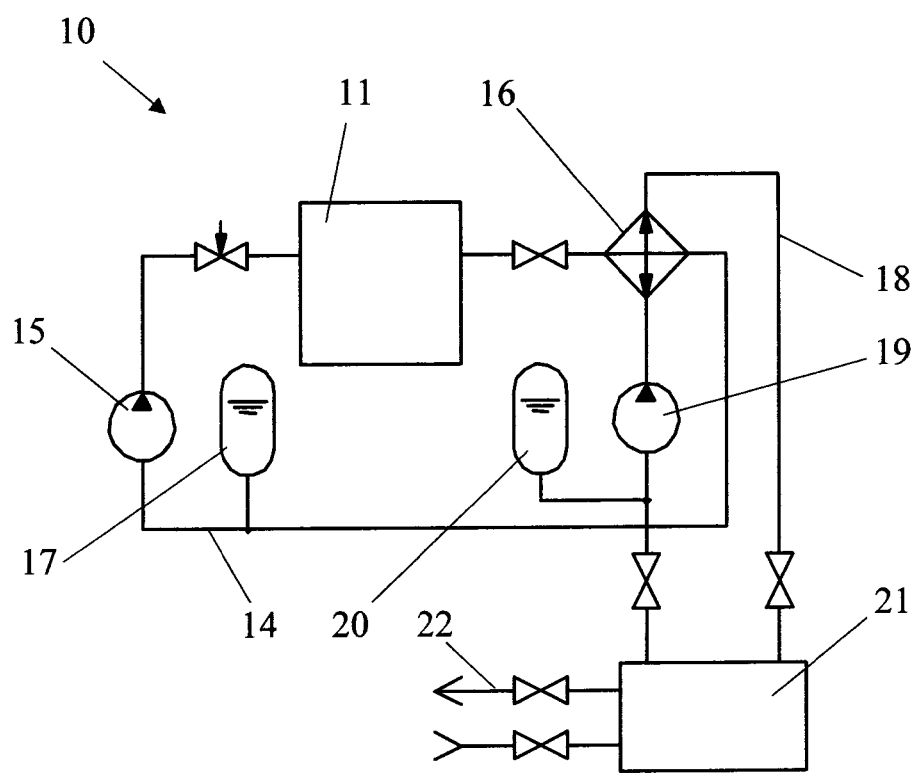
FIG. 3 shows a general view of the reactor core of a medical neutron source.
Figure 4:
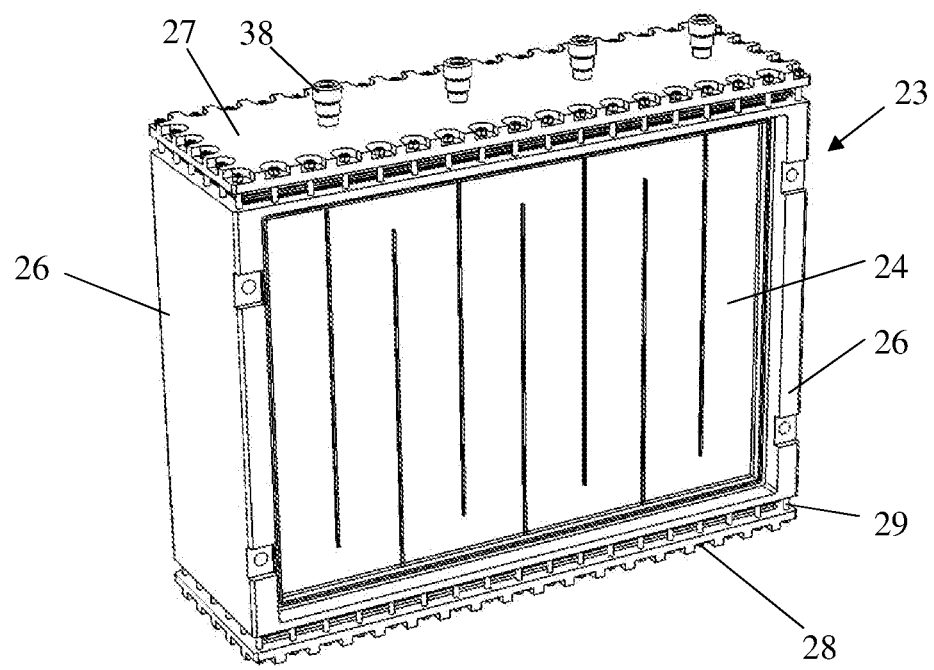
FIG. 4 is a view of the reactor core from the rear.
Figure 5:
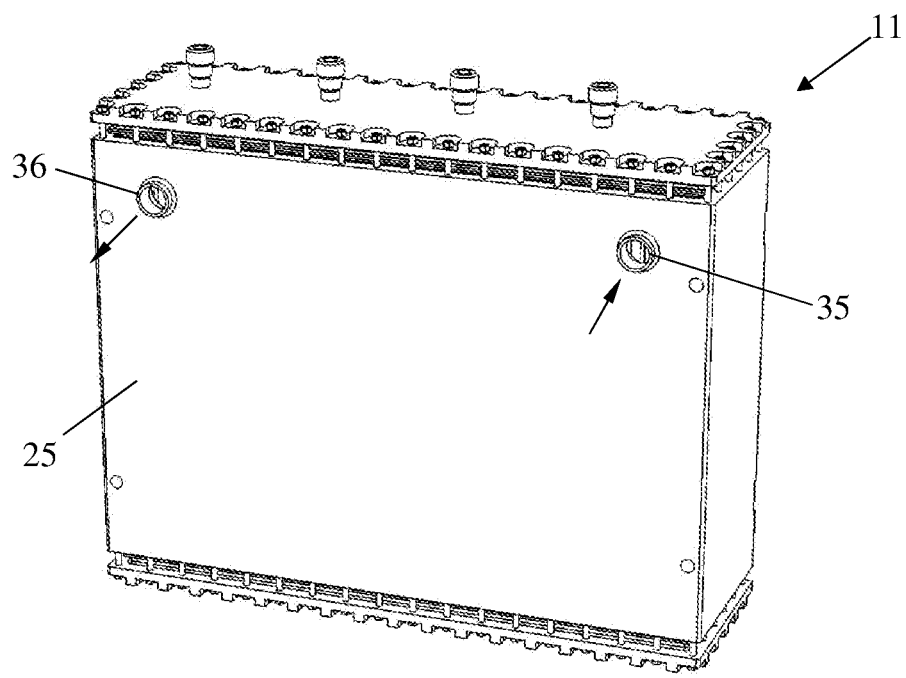
FIG. 5 shows a flow chart of the coolant in the core of the reactor.

A schematic diagram of the hydraulic system 10 is shown in FIG. 3. In the described embodiment, the nuclear reactor is a three-circuit reactor.

The first circuit 14 includes a core 11, a circulation pump 15, a heat exchanger 16 and a pressurizer 17. Water is used as the coolant of the primary circuit.

The second circuit 18 includes a circulation pump 19, a pressurizer 20, and a refrigeration unit 21. Water is also used as the primary coolant. Cooling of the refrigeration unit 21 is carried out by tap water, which runs through a third circuit 22.

The use of the refrigeration unit 21 in the second circuit allows to stabilize the temperature of the coolant at the entrance to the core 11 at 20° C. Stabilization of the inlet temperature of the coolant makes it possible to substantially reduce the changes in reactivity of the reactor at all stages of its operation.

The core of the reactor of the medical neutron source is shown in FIG. 4-7. The core 11 consists of a parallelepiped-shaped housing 23 with internal dimensions 494×397×120 mm. The core housing 23 has a front 24, a rear 25 and two side walls 26. The housing 23 is closed at the top and bottom, respectively, by a lid 27 and a bottom 28, which are connected by flanges to the housing by the studs 29. The housing 23 is sealed by welding the whiskers around the housing perimeter with the lid 27 and the bottom 28.

The upper supporting grid 30 and the lower distancing grid 31 are disposed on the housing 23. Upper ends 50 of fuel rods 32 are fixedly attached to the support grid 30. The fastening is carried out by means of a wire 33 threaded through the holes in the upper ends 50. Lower ends 51 of fuel rods 32 pass through the distancing grid 31. In this case, the lower ends 51 are able to move vertically with thermal expansion. Fuel rods 32 are located in a square grid with a pitch of 12×12 mm Since the length of fuel rods 32 is a small value of ~395 mm and, taking into account the low velocity of the coolant, only the grids 30 and 31 are used to separate the fuel rods 32 with no means of distancing in between.

Figure 6:
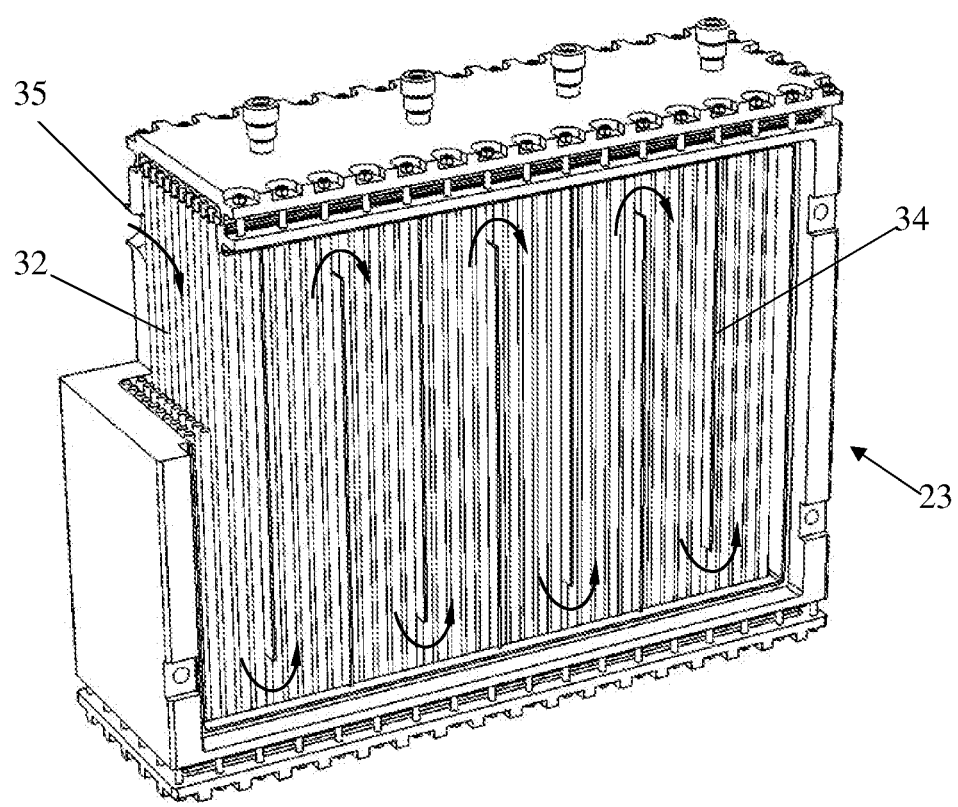
FIG. 6 shows a section through the reactor core.

In order to arrange the circulation of the coolant of the $1^{st}$ circuit, the housing 23 is divided by transverse partitions 34, which allow to obtain acceptable washing rates of fuel rods. Seven such partitions are installed in a "checkerboard" order with the formation of a labyrinth channel. FIG. 6 shows the flow pattern of the coolant in the core of the reactor (the front wall 24 is not shown). This core design makes it possible to obtain a uniform washing of fuel rods at acceptable rates.

In addition to the organization of the flow of the coolant, the baffles 34 play a force role, allowing a significant reduction in the thickness of the front wall 24 from the exit side of the neutron beam to 2 mm, which in turn allows increasing the neutron flux density at the exit from the core of the reactor. On the back wall 25 of the housing 23 there is a supply branch 35 and a branch pipe 36 for draining the coolant from the core 11.

Figure 7:
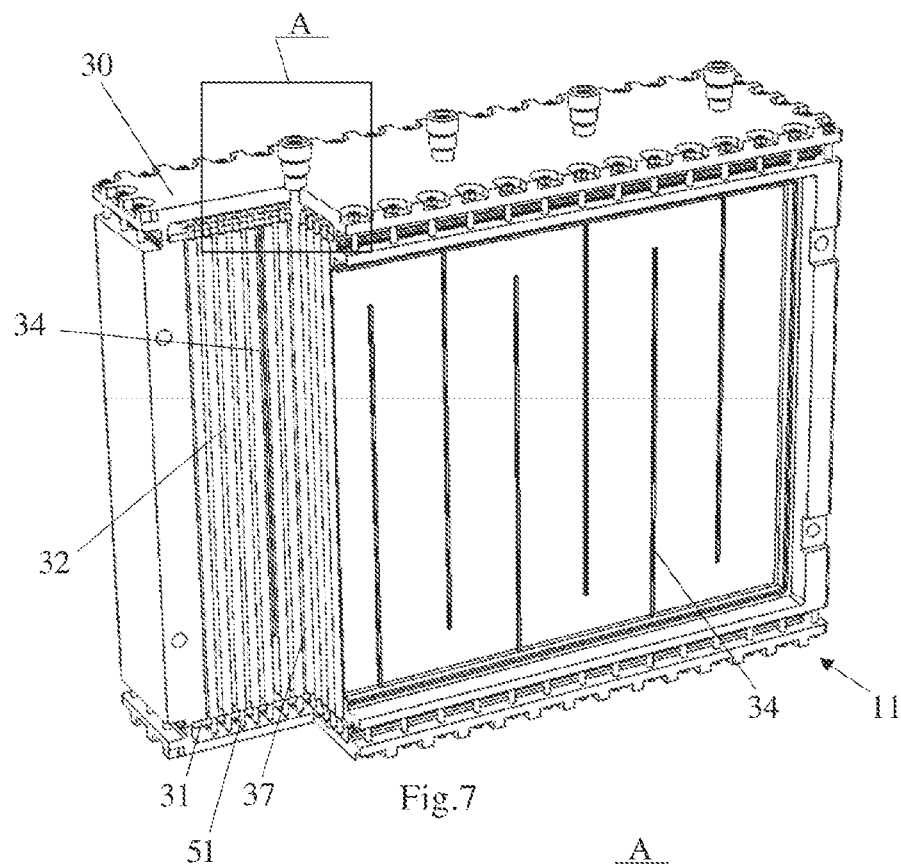
FIG. 7 shows a generalized hydraulic circuit of the reactor of a medical neutron source.
Figure 8:
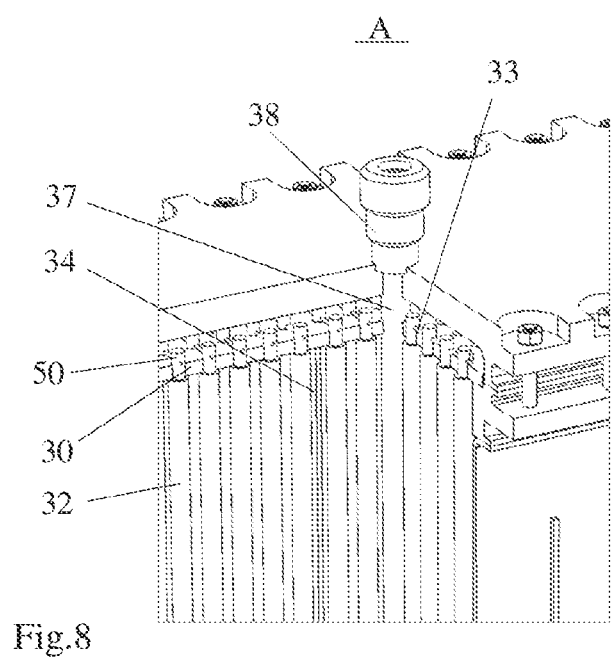
FIG. 8 shows view A of a generalized hydraulic circuit of the reactor of a medical neutron source.

On the cover 27 of the core housing, channels 37 are arranged to placement the CPS controls. As shown in FIG. 7 and FIG. 8, the channels 37 are located in the housing 23 instead of four fuel rods. The channels 37 are formed by pipes ø 10 mm with a wall thickness of 0.5 mm and terminate with threaded terminals 38 to which the movement mechanisms of the CPS controls are attached.

The reactor reflector 12 covers the core 11 from the rear, side, top and bottom sides and is divided into the rear, top, bottom and two side. The rear, upper, lower and side reflectors are made of stainless steel blocks (steel 12X18H10T) and have a total thickness of 300 mm each.

The protection of 3 reactors is subdivided into the front 39, the side 40, the rear 41, the top 42 and the lower 43 of the protection. As the basic materials of protection, borated polyethylene and depleted uranium are used, used in the form of blocks set by the ledge with overlapping joints of the blocks c to prevent the radiation "bursting".

The front protection 39 provides the required dose situation in the medical box at the outlet of the NCT beam and in adjacent rooms. The frontal protection 39 in the direction of the NCT beam output includes:
a) the filter itself, which performs both protective functions;
b) lead collimator, also carrying protective functions (mainly from gamma radiation); the thickness of the conical part of the collimator is 150 mm, the thickness of the cylindrical part is 100 mm;
c) a multilayer protective composition (away from the core) of depleted uranium (U) and borated polyethylene (PB):

PB (400 mm)+U (220 mm)+PB (130 mm)+U (20 mm)

Side protection 40 provides the required dose situation in the medical box at the FNT beam outlet and in adjacent rooms. The side protection in the direction of the FNT beam output consists of:
a) a steel reflector 300 mm thick;
b) a multilayer structure of depleted uranium and borated polyethylene (in the direction away from the core):

U (100 mm)+PB (300 mm)+U (200 mm)+PB (150 mm)+U (30 mm)

The side protection in other directions by composition and structure is similar to the upper 42 and lower 43 protections. This is a three-layer composition of the following composition:

U (100 mm)+PB (500 mm)+U (100 mm)

Rear protection 41 is designed to protect other rooms adjacent to the reactor.

The rear protection structure includes a steel reflector (300 mm) and a three-layer composition:

U (120 mm)+PB (900 mm)+U (100 mm)

Channel 4 for the neutron-capture therapy is formed by aperture 44 in the front shield located coaxially with the conical hole of the lead collimator 8.

The channel 5 for the fast neutron therapy is formed by a through hole 45 in the side shield and the side reflector.

The first movable gate 6 allows blocking the neutron beam of NCT, when a neutron therapy session takes place on the FNT beam. In this case, to minimize the neutron background at the location of the fast neutron therapy patient, a plug 46 of borated polyethylene is introduced into the channel of the NCT beam.

The second movable gate 7 allows the beam to be blocked by the FNT during irradiation on the NCT beam. In this case, a plug 47 of borated polyethylene is also added to the FNT channel. When the reactor is shut down, both beams are blocked by sliders and in the channels there are corks of borated polyethylene.

The CPS 13 of the reactor system includes four control rods 32. The rods are moved through dry channels 37 using actuators 48. The neutron absorbing material of the control rods—boron carbide (B4C) is placed inside cylindrical rods 7 mm in diameter and with a shell thickness of 0.3 mm.

In order to place the actuators 48 of the CPS movement mechanisms in the upper protection 42 and the upper reflector, channels are made. In the rear protection 41 and in the rear reflector, channels are arranged for placing conduits 49 of the first circuit connected to the supply branch pipe and the outlet for the coolant to the core.

The operation of a medical neutron source to minimize the number of attendants and to minimize the accumulation of radioactive waste is carried out in a "start-stop" mode, implying the operation of the reactor at rated power only during a therapy session for about one hour.

The operation of the reactor on power is needed for approximately 3 hours per day for irradiation of 1-2 patients. Taking into account the preparatory, starting and stopping operations, the time for the service shift will be 5-8 hours. For the rest of the time (at night or weekends), the reactor is put into temporary shutdown mode. The presence of supervisory personnel during the temporary stop is not required.

To carry out the neutron therapy, a medical neutron source is used as follows. A coolant with a temperature of 20° C. is supplied to the core of the nuclear reactor in the subcritical state, where the water is used.

The core of the nuclear reactor is withdrawn from subcritical to critical before the nominal power of the nuclear reactor is reached. Transfer of the core from the subcritical state to the critical one is carried out by removing one of the CPS control rods from the core.

The patient is placed in front of the necessary neutron exit channel. The choice of a specific neutron output channel is determined by the indications of an oncological disease. After that, the neutron output channel is opened for the neutron therapy session. During the time of the neutron therapy session, the operation of the reactor at rated power is maintained.

At the end of the neutron therapy session, the neutron exit channel is simultaneously closed and the reactor core is transferred to a subcritical state. The core is transferred from the critical state to the subcritical one by introducing one of the CPS control rods into the core.

The temperature of the coolant at the entrance to the core is kept constant and equal to the set temperature, both during the core withdrawal to the critical state and during the operation of the nuclear reactor at rated power.

The daily schedule for the operation of the reactor of a medical neutron source in the therapy of 2 patients may be as follows:

| | |
|---|---|
| checking systems and equipment, turning on circulation on the contours, the reactor output to a power of 0.1-0.5 kW at a stable temperature regime | 2 hours, |
| Preparation of the patient for irradiation | 0.5 hours, |
| irradiation session with a power output up to 10 kW | 0.3-1 hour, |
| patient replacement (power 0.1-0.5 kW) | 1 hour, |
| irradiation session with a power output up to 10 kW | 0.3-1 hour, |
| reactor shutdown, patient removal | 0.3 hour, |
| cooling down, setting the mode temporary stop | 1 hour. |
| Total | 5.4-6.8 hours. |

After a double irradiation session, the reactor is silenced by all CPS controls, the set time is damped, then the chiller and technological systems are shut down. The reactor is left in this state until the next working day.

While various aspects and embodiments of this invention have been described herein, specialists in this sphere of technique will understand that other approaches to the implementation of this invention are possible. Various aspects and embodiments of the present invention are set forth herein for illustrative purposes and are not intended to be limiting, and the scope of protection of the present invention is set forth in the following claims.

What is claimed is:

1. A medical neutron source comprising:
    a nuclear reactor comprising:
        a core formed by a flat housing shaped as a parallelepiped, the housing having a front wall, a rear wall, two side walls, a lid, and a bottom;
        a neutron reflector covering having a rear reflector, two side reflectors, a top reflector and a bottom reflector, and covering the rear wall, the two sides walls, the lid, and the bottom of the core, respectively, wherein the front of the core is free from the neutron reflector covering;
        an upper supporting grid and a lower distancing grid, both grids being disposed on the housing;
        fuel rods comprising upper ends and lower ends, the upper ends of the fuel rods being immovably fixed to the upper supporting grid, wherein the fuel rods are capable of experiencing thermal expansion, and wherein the lower ends of the fuel rods extend through the lower distancing grid and are capable of vertically moving when the fuel rods thermally expand;
        the housing lid having channels disposed on the lid with controls of a control and protection system (CPS controls);
        disposed on the housing a supply pipe and a discharge pipe of a coolant of a primary circuit of a hydraulic system;
        partitions separating an internal volume of the housing to ensure washing over of the fuel rods and the channels with CPS controls by the coolant;
    a collimator with a hole shaped as a truncated cone;
    a neutron filter placed in the hole of the collimator in such a way that a larger diameter of the truncated cone hole is adjacent to the front wall of the housing of the core of the reactor;
    a protection that covers the neutron reflector covering and the collimator, the protection being subdivided into a front protection, rear protection, two side protections, top protection and bottom protection;
    a neutron capture therapy channel formed by a hole in the front protection, the hole being coaxial with the hole of the collimator;
    a fast neutron therapy channel formed by a through hole in the side protection and the side reflector;
    a first movable gate that opens and closes the neutron capture therapy channel; and
    a second movable gate that opens and closes the fast neutron therapy channel.

2. The medical neutron source according to claim 1, wherein the primary circuit comprises a circulation pump, a heat exchanger and a pressurizer.

3. The medical neutron source according to claim 2, wherein the circulation pump, the heat exchanger, and the pressurizer connected to a hydraulic circuit are located outside of the protection.

4. The medical neutron source according to claim 1, wherein the rear protection and the rear reflector comprise openings for disposing the supply pipe and the discharge pipe.

5. The medical neutron source according to claim 1, wherein the housing lid is provided with at least four openings for placing CPS controls.

6. The medical neutron source according to claim 5, wherein the openings are provided with threaded connections with associated actuators.

7. The medical neutron source according to claim 6, wherein the top protection and the top reflector comprise openings for disposing the actuators for moving the CPS controls.

8. The medical neutron source according to claim 7, wherein at least four control rods are used as the CPS controls, the at least four control rods being movable by the actuators the channels for the CPS controls.

9. The medical neutron source according to claim 7, wherein one of the control rods is a regulator for providing a rated power of the nuclear reactor.

10. The medical neutron source according to claim 1, wherein uranium dioxide ($UO_2$) with $^{235}U$ enrichment selected from an interval of 15% to 20% is used as fuel in the fuel rods.

11. The medical neutron source according to claim 1, wherein $B_4C$ is used as an absorbing material of the control rods.

12. The medical neutron source according to claim 1, wherein Pb is used as a collimator material.

13. A method of using a medical neutron source comprising:
    providing the medical neutron source of claim 1;
    supplying the coolant at a predetermined temperature to the core of the nuclear reactor, the core being in a subcritical state;
    transitioning the core of the nuclear reactor from the subcritical state to a critical state until a rated power of the nuclear reactor is reached;
    opening the neutron capture therapy channel or the fast neutron therapy channel for a neutron therapy session;
    supporting operation of the nuclear reactor at a rated power during the neutron therapy session; and
    simultaneously closing the neutron therapy channel used in the neutron therapy session and transferring the core to the subcritical state after completion of the neutron therapy session while maintaining the temperature of the coolant at an entrance to the core unchanged and equal to the predetermined temperature both during transitioning the core to the critical state and during operation of the nuclear reactor at the rated power.

14. The method of claim 13, wherein water is used as the coolant.

15. The method of claim 14, wherein the predetermined temperature of the water at the entrance to the core is selected from an interval of from 18° C. to 24° C.

16. The method of claim 15, wherein transitioning the core from the subcritical state to the critical state and from the critical state to the subcritical state, respectively, comprises removing one of the CPS control rods from the core or moving one of the CPS control rods into the core.

* * * * *